United States Patent [19]

Henley

[11] Patent Number: 5,504,438
[45] Date of Patent: Apr. 2, 1996

[54] TESTING METHOD FOR IMAGING DEFECTS IN A LIQUID CRYSTAL DISPLAY SUBSTRATE

[75] Inventor: Francois J. Henley, Los Gatos, Calif.

[73] Assignee: Photon Dynamics, Inc., Milpitas, Calif.

[21] Appl. No.: 757,467

[22] Filed: Sep. 10, 1991

[51] Int. Cl.$^6$ .................................................. G01R 31/22
[52] U.S. Cl. ........................................ 324/770; 324/158.1
[58] Field of Search ................................ 324/158 R, 96, 324/73.1, 770, 158.1, 760, 753, 750; 382/8; 358/106, 107; 359/215, 248; 257/48; 345/87; 348/126

[56] References Cited

U.S. PATENT DOCUMENTS

| | | |
|---|---|---|
| 3,889,053 | 6/1975 | Lloyd et al. |
| 3,934,199 | 1/1976 | Channin ........................... 324/158 R |
| 3,992,663 | 11/1976 | Seddick ................................. 324/52 |
| 4,242,635 | 12/1980 | Burns .............................. 324/158 R |

(List continued on next page.)

FOREIGN PATENT DOCUMENTS

| | | |
|---|---|---|
| 3111393A1 | 9/1982 | Germany. |
| 55-56330 | 4/1980 | Japan. |
| 55-58893 | 4/1980 | Japan. |

OTHER PUBLICATIONS

Achieving ATE Accuray At Gigahertz Test Rates: Comparison of Electronic and Electro–Optic Sampling Technologies, F. J. Henley, H. J. Choi, Int'l Test Conf. Aug., 1989.

Systems Solutions Based on Electro–Optic Sampling to High Speed IC Test Problems, F. J. Henley, D. B. MacDonald, SPIE vol. 795 Characterization of Very High Speed Semiconductor Devices & Integrated Circuits (1987) pp. 345–351.

Characterization of High Speed (Above 500 MHz) Devices Using Advanced ATE–Techniques, Results and Device Problems, S. Barton, Proceedings of the IEEE 1989, Int'l Test Conf., Aug. 1989.

In–Process Testing of Thin Film Transistor Arrays; R. Wisnieff et al.; SID 90 Digest pp. 190–193.

NCAP Displays: Optical Switching and Dielectric Properties; L. Welsh et al.; SID 90 Digest; pp. 220–223.

Testing and Qualifications of A–Si TFT–LC Color Cells for Military Avionics Applications; F. C. Luo et al.; SID 90 Digest; pp. 194–196.

Hitachi LCD Advertisement; pp. 2 and 3.

Measurement of Electro–Optic Characteristics of LCDs; M. E. Becker et al.; SID 90 Digest; pp. 163–166.

Testing and Qualificastionsof A Si TFT–LC Color Cells for Military Avionics Applications; F. C. Luo et al; SID 90 Digest; pp. 194–196.

Using Electro–Optic Sampling Technology For Accurate Gigahertz ATE: Overview of the Art, Francois J. Henley, 1990 IEEE VLSI Test Symposium.

(List continued on next page.)

Primary Examiner—Vinh P. Nguyen
Attorney, Agent, or Firm—Townsend and Townsend Khourie and Crew

[57] ABSTRACT

A method for testing liquid crystal display substrates with use of a testing apparatus which includes an electro-optical element. The test protocol includes applying a voltage between the circuitry on the liquid crystal display and the electro-optical element, irradiating the electro-optical element, evaluating performance under a variety of voltage conditions, and evaluating the corresponding response characteristics of the electro-optical element. The response characteristics are recorded by a plurality of CCD devices, each recording a different section of the panel. The changes in the magnitude of impressed voltage and polarity are synchronized with the recording timing. The recorded data is stored as frame memory which is subjected to frame by frame analysis to obtain quantitative information regarding the status of defective pixels. The resulting data is synthesized to obtain a composite performance picture of the entire panel which can be displayed as a unit to quickly obtain quantitative information regarding the overall defect presence. The technique is independent of the screen size, since the final large size screen image can be constructed from a plurality of smaller screens.

18 Claims, 3 Drawing Sheets

U.S. PATENT DOCUMENTS

| | | | |
|---|---|---|---|
| 4,355,278 | 10/1982 | Burns et al. | 324/158 R |
| 4,368,523 | 1/1983 | Kawate | 365/63 |
| 4,444,801 | 4/1984 | Hongo et al. | 427/10 |
| 4,463,073 | 7/1984 | Miyauchi et al. | 430/5 |
| 4,465,969 | 8/1984 | Tada et al. | 324/96 |
| 4,507,605 | 3/1985 | Geisel | 324/73 |
| 4,510,222 | 4/1985 | Okunaka et al. | 430/5 |
| 4,523,847 | 6/1985 | Bjorklund et al. | 356/349 |
| 4,542,333 | 9/1985 | Koontz | 324/52 |
| 4,563,093 | 1/1986 | Tada et al. | 356/368 |
| 4,618,819 | 10/1986 | Mourou et al. | 324/77 |
| 4,631,576 | 12/1986 | St. John | 358/65 |
| 4,633,242 | 12/1986 | Sekiya | 340/719 |
| 4,636,403 | 1/1987 | Fisanick et al. | 427/53 |
| 4,688,900 | 8/1987 | Doane et al. | 350/347 |
| 4,727,234 | 2/1988 | Oprysko et al. | 219/121 |
| 4,758,092 | 7/1988 | Heinrich et al. | 356/36 |
| 4,776,022 | 10/1988 | Fox et al. | 382/8 |
| 4,819,038 | 4/1989 | Alt | 357/4 |
| 4,825,201 | 8/1989 | Watanabe et al. | 340/717 |
| 4,855,591 | 8/1989 | Nakamura et al. | 250/225 |
| 4,862,075 | 8/1989 | Choi et al. | 324/158 R |
| 4,868,492 | 11/1989 | Beha et al. | 324/73 |
| 4,870,357 | 9/1989 | Young et al. | 324/158 R |
| 4,875,006 | 10/1989 | Henley et al. | 324/158 R |
| 4,899,105 | 2/1990 | Akiyama | 324/158 |
| 4,906,922 | 6/1990 | Takahashi et al. | 324/158 R |
| 4,910,458 | 3/1990 | Forsyth et al. | 324/158 |
| 4,944,576 | 7/1990 | Lacker et al. | 350/334 |
| 4,983,911 | 1/1991 | Henley | 324/158 R |
| 4,999,577 | 3/1991 | Beha et al. | 324/158 |
| 5,017,755 | 5/1991 | Yahagi et al. | 219/121 |
| 5,037,683 | 7/1991 | Takahashi et al. | 324/158 |
| 5,043,297 | 8/1991 | Suzuki et al. | 437/51 |

OTHER PUBLICATIONS

High Speed Pattern Generator and GaAs Pin Electronics For a Gigahertz Production Test System, D. J. Kratzer, S. Barton, F. J. Henley D. A. Plomgrem, Proceedings of IEEE 1988 Int'l Test Conf, Sep. 1988.

Test Head Using Electro–Optic Receivers and GaAs Pin Eloectronics for a Gigahertz Production Test System, F. J. Henley, H. J. Choi, Proceedings of IEEE 1988 Int'l Test Conference, Sep. 1988.

System Tests Devices at GHz Rates, Lyle H. McCarty, Design News, Apr., 10, 1989.

Electro–Optic Device Tester Tops 1 GHz, John Novellino, Electronic Design, Sep. 8, 1988.

An Ultra High Speed Test System, Francois J. Henley, IEEE Design & Test of Computers, Feb. 1989.

Electro–Optic Technology Supports Gigahertz Speeds; Francois J. Henley, Electronics Test, Sep. 1988.

TESTING METHOD FOR IMAGING DEFECTS IN A LIQUID CRYSTAL DISPLAY SUBSTRATE

BACKGROUND OF THE INVENTION

In recent years color televisions featuring liquid crystal (hereinafter referred to as LC) display screens have become practical. LC-based color panels consist of a quartz substrate having a matrix of thin film transistors (TFT) made from polycrystalline silicon, and an LC display substrate which is constructed by laminating a transparent filter glass substrate on top of the quartz substrate and sealing liquid crystal in the small gap between the quartz substrate and the glass plate. The functional characteristic of the LC-display is a twisted nematic mode. For imaging applications, the active-matrix driven display circuit arrangement is advantageous because of its adaptability to large area devices and to a high density of pixels and other circuit components. Practical applications have been implemented starting with relatively small display devices.

Such active-matrix driven LC panels are produced according to the following procedure. A transparent glass plate is placed, together with an intervening spacer, on top of a completed LC display substrate, and the small gap is filled with liquid crystal and sealed. LC display substrates usually contain as many as 250,000–500,000 pixels and more recent ones contain over 1,000,000 pixels.

Thin film processing steps are carried out in clean rooms to prevent small dust particles from causing problems in fabrication. However, as circuit density increases, even the minute amount of micron-sized dust particles, present naturally in the processing environment, are potential sources of open or short circuit defects for these micron size pixels and lines. The present standards allow up to ten such display defects per substrate, and those panels containing beyond this number are rejected. In other words, this number is the lowest defect level achievable by the present technology. As the panel becomes larger, the number of defects increases correspondingly, and the number of rejects increases accordingly. This is one reason for the high cost of large screen LC display devices, but the problems are further compounded by the difficulties associated with testing of such a large number of pixels.

The methods of testing pixels in LC display devices include the probing method, but this technique is inappropriate for such a large number of test objects which would require a large amount of costly testing time and effort. For this reason, the substrates are not tested during processing, but each substrate is visually evaluated by operating the display after it has been finish assembled into a display panel. At this late stage of manufacturing, even if imaging defects are discovered, the defective panels cannot be reprocessed. They are treated as rejects, and constitute a major reason for the poor yield of LC display devices. Further, visual inspection can only be qualitative and important quantitative information which could lead to process improvement is lacking.

SUMMARY OF THE INVENTION

The method of the present invention utilizes a LC display substrate containing a plurality of pixels arranged in a matrix and an array of electro-optical elements disposed on a separate array plate opposing the top surface of the substrate. The testing process includes the steps of: impressing a voltage between the electro-optical elements and the pixels; irradiating the said electro-optical elements to cause a change in the output response of said electro-optical elements; evaluating the performance of said electro-optical elements under varied magnitude of voltage and polarity; and evaluating the corresponding imaging characteristics of said electro-optical elements to the varied stimulations. The imaging characteristics are evaluated by a plurality of recording devices, each of which records the imaging responses of separate sections of the substrate. The recordings are synchronized with the application of the changes in the magnitude of impressed voltage and polarity. The recorded data is stored as frame memories and is subsequently analyzed frame by frame to obtain quantitative information on the status of defective pixels in the entire LC display substrate.

According to the present invention, successive frame data containing the responses of every pixel in the substrate to the synchronized application of varied voltage and polarity, is stored in memory. The data is subjected to frame by frame analysis, and the resulting frame data is synthesized to obtain a composite picture of the performance of the entire panel to quickly obtain quantitative information regarding overall defect presence.

The present invention was developed in order to overcome such problems associated with the present techniques of testing LC display pixels.

DESCRIPTION OF A PREFERRED EMBODIMENT

Figure 1:
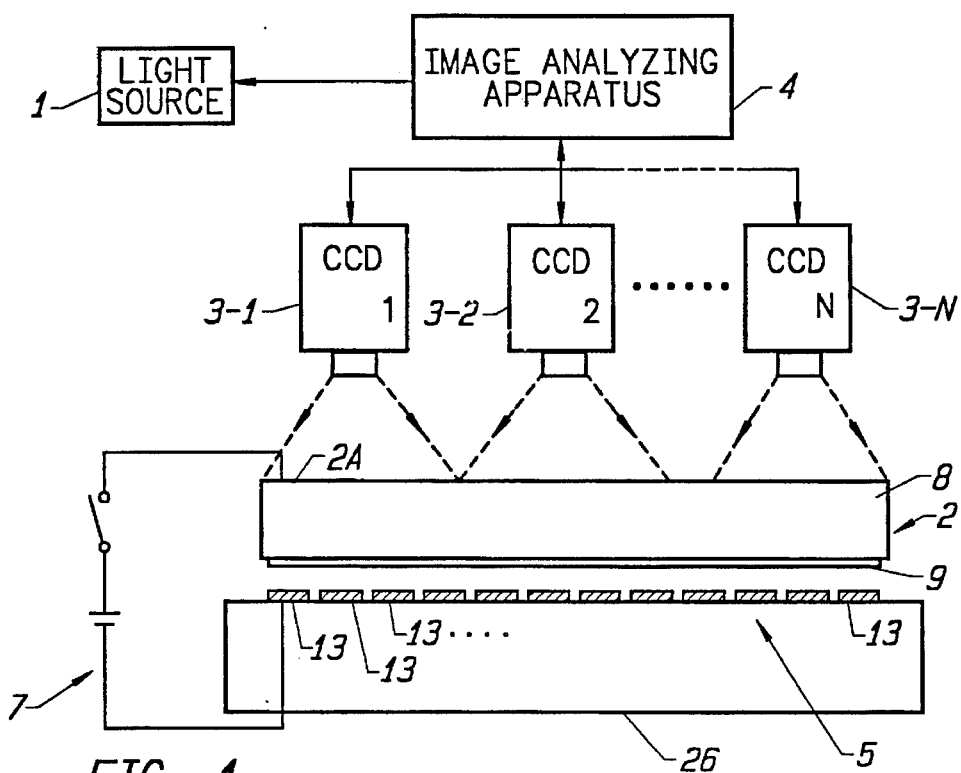
FIG. 1 is a schematic diagram of the main parts of the testing apparatus in an embodiment.

The preferred embodiment of the present invention will be explained with reference to the drawings. FIG. 1 is a block diagram showing the main components of the testing apparatus in one preferred embodiment. Light source 1 is a halogen or LED lamp. An electro-optical array plate 2 having an array of elements which changes the plate's irradiation response characteristics when an electric field is applied. This array plate 2 is composed of an LC sheet 8 with sealed-in polymer-dispersed liquid crystal of high molecular weight and a non-conductive reflective surface 9 disposed on the bottom surface of said sheet 8, and a transparent thin film electrode 2a disposed on the top surface of said sheet 8. The recording devices are CCD cameras, designated by numbers 3-1, 3-2 up to 3-N cameras, which can be arranged in such a way to record the entire area of the electro-optical array plate 2. The video signals recorded by the camera 3-1 through 3-N are analyzed by an image analyzing apparatus 4, which produces a composite screen of the overall defect status, including the quantity and the distribution of defects in the LC display substrate 5. The details of this image analyzing apparatus 4 will be provided later.

Figure 2:
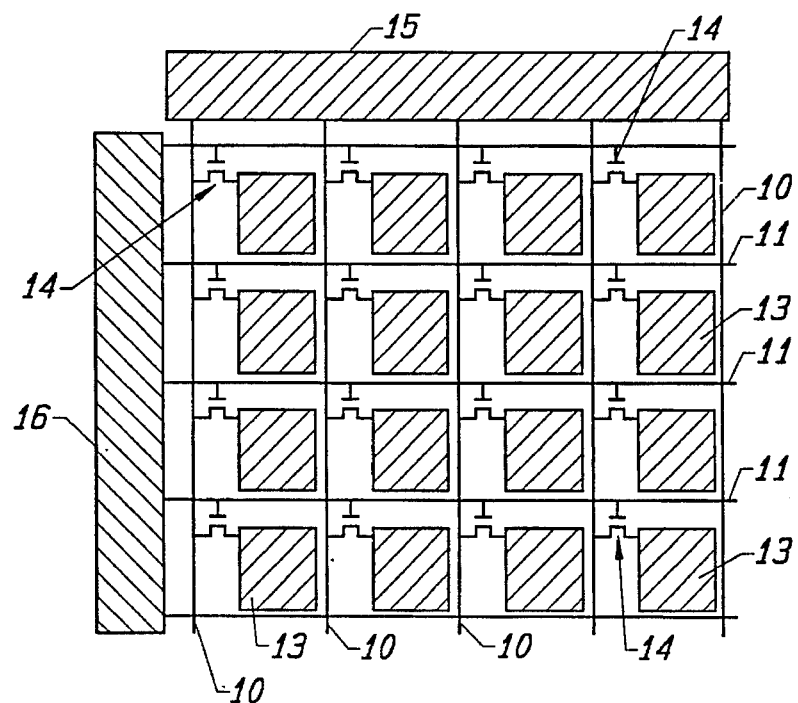
FIG. 2 is an illustration for the construction of the LC display substrate in the same embodiment.

The LC display substrate 5 is placed on top of table 26. The main components of the LC display substrate 5 are as shown in FIG. 2, and consist of a matrix of thin film transistors (TFT) 14, the source electrodes of which are connected to common source lines 10 which form a matrix with gate lines 11 to which the gate electrodes of the TFT are commonly connected. The drain electrode of TFT 14 is connected to a respective pixel electrode 13. Shorting bars 15 and 16 are for the purpose of preventing damage to TFT 14 caused by static electricity, and are fabricated during the substrate preparation stage and are removed when the process is completed. Voltage source 7 impresses a bias voltage between transparent thin film electrode 2a and pixel electrodes 13 on substrate 5. Shorting bars 15 and 16 are employed for the purpose of applying signals to gate 11 and drain lines.

To simplify the presentation, the description is provided for one CCD camera from among the many cameras 3-1 to 3-N. The remaining cameras duplicate the action of the one camera.

First, a bias voltage of a suitable level is applied between the transparent electrode 2a and the pixel electrodes 13. A constant voltage will be impressed uniformly across the electro-optical array plate 2 when there are no abnormalities in the substrate 5. Abnormalities such as a short or open circuit in the source lines 10 or gate lines 11 will result in a non-uniform voltage distribution. The LC molecules align themselves in one direction under the influence of the electric field created by the electro-optical array plate 2, and the LC sheet 8 becomes transparent to light. Under this condition if the light source 1 is turned on, the light passing through the LC sheet 8 is reflected by the reflective surface 9, and the camera 3 records an image having uniform brightness.

If a pixel is defective, the transmissivity of the electro-optical array plate 2 in the region corresponding to this pixel changes. As a result, CCD 3 records an image having bright spots and dark spots corresponding to normal and malfunctioning pixels, respectively. The image analyzing apparatus 4 scans such images and constructs and displays information on defective pixels such as their quantity and distribution.

The field of view of a single camera is not sufficient to cover a large display area. Therefore, a multi-camera system was developed to deal with such a situation so that a large screen frame can be synthesized from several small camera frames covering small sections. The operation of this apparatus 4 is described next.

Figure 3:
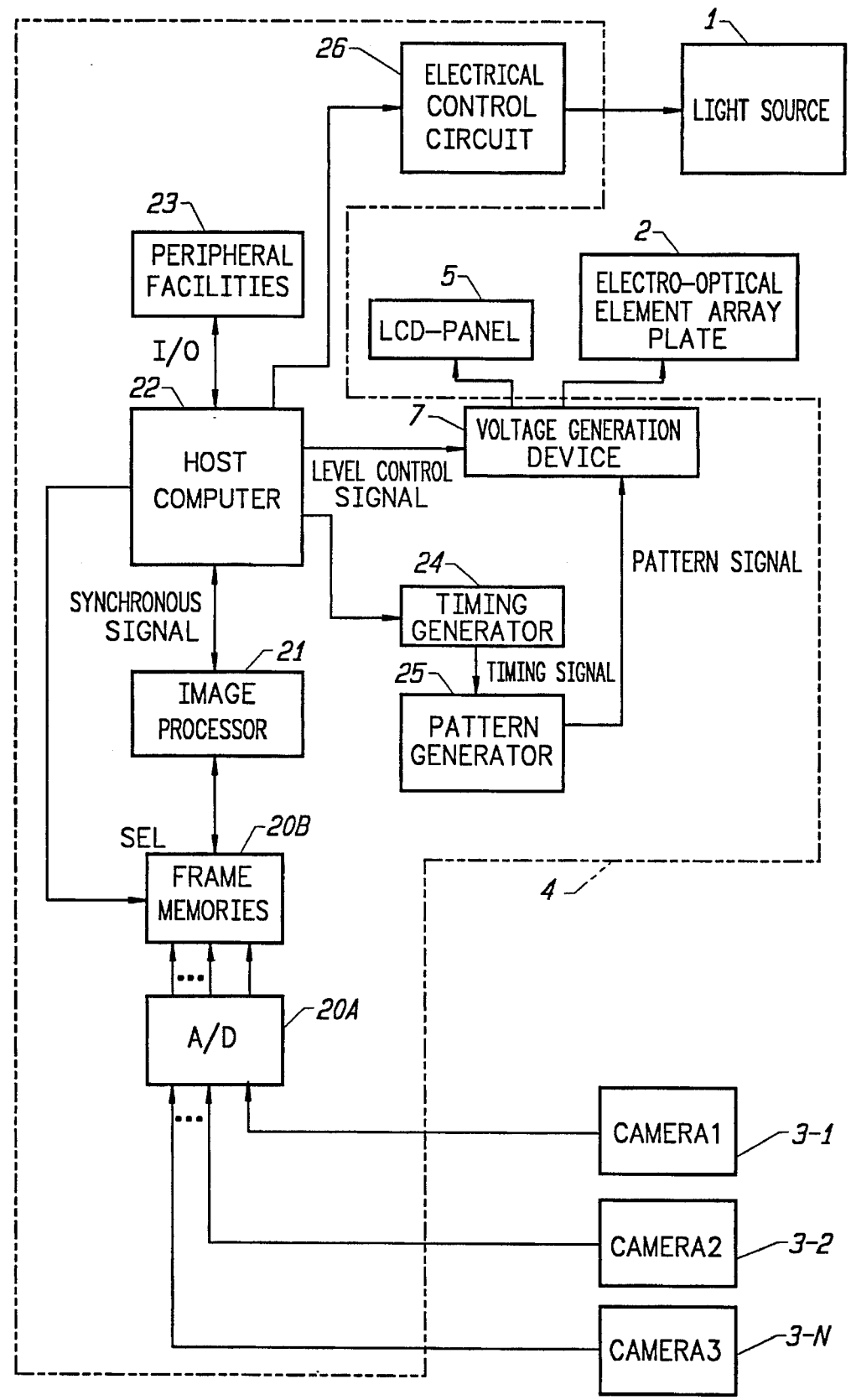
FIG. 3 is a block diagram of the main parts of the image frame processing device in the same embodiment.

The image analyzing apparatus 4 is explained with reference to FIG. 3. In this figure, those parts which are the same as in FIG. 1 are given the same reference number and their explanations are omitted.

Reference number 20a refers to A/D converters which convert the video signals generated by each of the cameras 3-1 to 3-N into digital signals. The, output data from the A/D converters 20a are stored in the frame memory 20b in the form of frame memories for each of the cameras 3-1 to 3N. The memory data is switched from one camera to another among the banks by means of the bank switching signals (SEL), in which each bank stores data from an assigned camera. The image processor 21 accepts successive frame data from the memory banks provided by the scanning signal SEL, and prepares the data to generate image data for each frame. This pretreatment includes such steps as synthesizing four frames into one scene, and treats the frame data in order to eliminate noise and to convert them to binary data.

The overall process is controlled through a host computer 22 which provides control functions to various components as well as provides an image processing function to the data forwarded from the image processor 21. This host computer 22 also supplies bank switching signal SEL to memory banks 20b. Reference number 23 refers to peripheral facilities such as a keyboard, a display device, and external memory units. The results of the processed image supplied by the host computer 22, that is the status of defects in LC substrate 5 is displayed on this display device.

Timing device 24 generates and outputs synchronizing signals to control the recording timing of each frame in accordance with the video signal generated by the host computer 22. A pattern generator 25 generates certain patterns according to the output from the timing device. This pattern controls the polarity of the biasing signal to be impressed on the pixel electrodes 13, for each frame recording event. For example, to record one scene consisting of four successive frames, the polarity of the sequential recording is changed in the order of +, −, −, +.

Voltage generation device 7 generates the biasing voltage specified by the host computer 22 and applies this biasing voltage between the pixel electrode 13 and the transparent electrode 2a in accordance with the polarity sequence as above. Reference number 26 refers to electric power control circuit to control electric power supplied to the light source 1.

Figure 4:
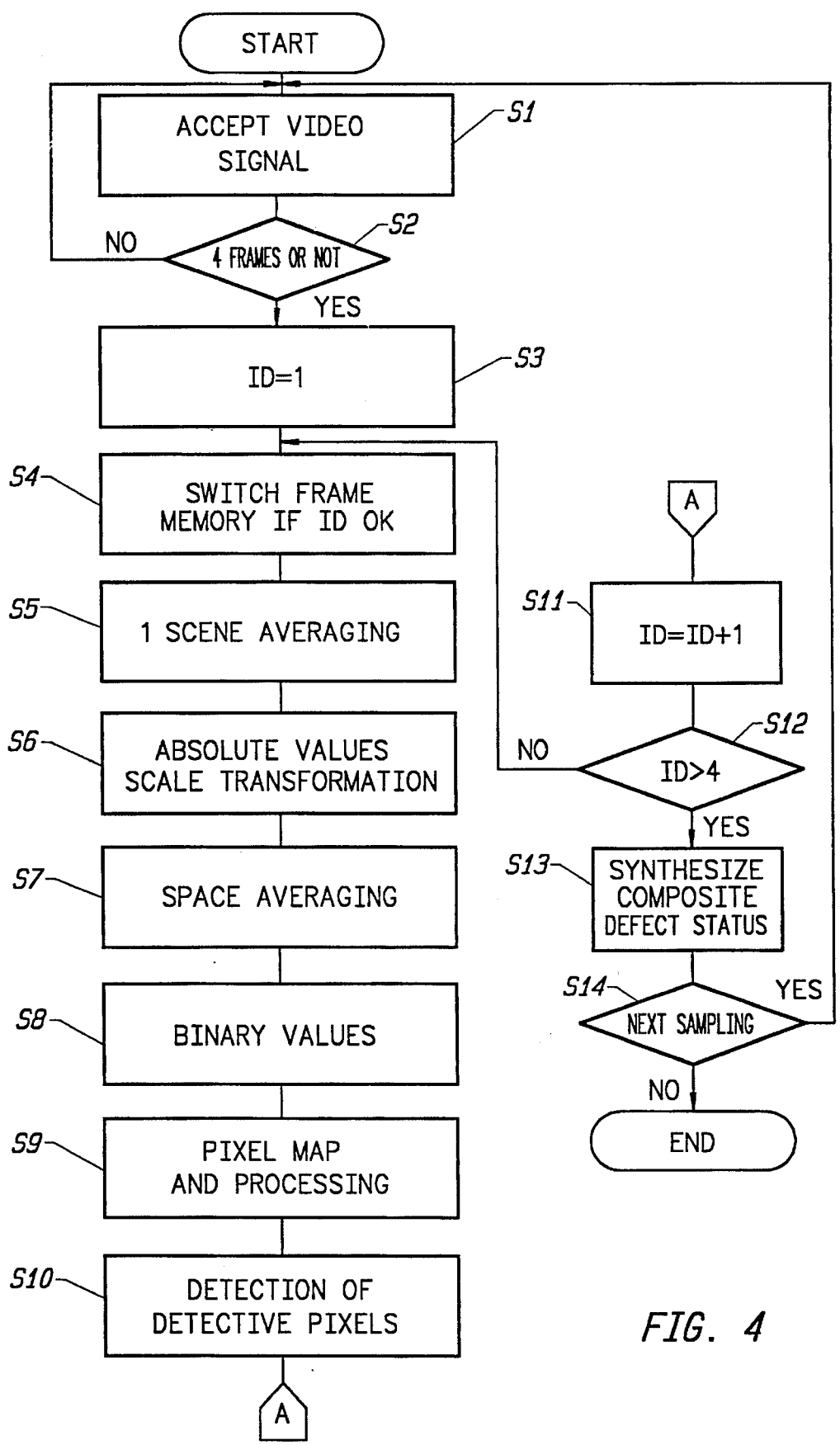
FIG. 4 is a flow chart to explain the logical flow of the computer aided system and process of the testing apparatus.

The testing operation is further explained in reference to FIG. 4, using the setup shown in FIG. 1. When the image analyzing apparatus 4 is turned on, the host computer 22 executes necessary programs to initialize all the programs and registers, and stands by for further instructions. The operator (of the test apparatus) activates the switch to put the apparatus in the setting mode to provide control signals to the various components, during which initial condition setting of the light source 1, CCD cameras 3 and the voltage generating device 7 is performed. This step includes offset and gain calibrations. The offset calibration is to determine the initial brightness of each pixel in the condition that no voltage is impressed on the pixel electrode. In the gain calibration step, the value of the brightness for each pixel is determined with the application of preset biasing voltage, and the gain (brightness) value is obtained by subtracting the offset value from the gain value to obtain brightness corresponding to the biasing voltage.

After the above preliminary steps, the operator activates the "Test Start" switch (not shown) provided on the analyzing apparatus 4 to begin a series of testing steps as shown by the flow chart shown in FIG. 4. This is an example of testing using four CCD cameras 3-1 to 3-4.

In step S1, cameras 3-1 through 3-4.start recording and the video signals equivalent to one frame, after going through A/D conversion, are stored in frame memory 20b. In step S2, the program checks for the presence, in each bank, of frame data sufficient for four frames. In this case, since there is data for only one frame, the path goes to "NO" and the program returns to step S1 to repeat the process. The process between the steps S1 and S2 continues until all frame data to satisfy four frames have been taken.

If the four data frames are designated by frame A, frame B, frame C and frame D, and the biasing voltage of the magnitude and polarity discussed above is applied between the pixel electrode 13 and the transparent electrode 2a. That is, during recording of frame A, the biasing voltage is +5 V; for frame B, −5 V; for frame C, −5 V; and for frame D, +5 V.

In the next step S3, the host computer 22 sets "1" as the identification number ID for the camera 3-1, in order to distinguish various cameras 3-1 to 3-4, in preparation for generating the bank switching signal SEL. In step S4, the bank switching step is carried out in the frame memory 20b, according to the required ID number. That is, the frame memory 20b is supplied with a signal to switch banks, and as a result, the frame data for four frames are taken into the image processor 21. The program then proceeds to step S5.

In step S5, the data from four frames is treated as data for one scene, and all of the data is subjected to averaging treatment. This treatment removes the drift component from the frame signals, which is caused by the linear increase in the light transmissivity of electro-optical elements during the recording time lapse of one scene. In order to remove such excess brightness values which are added to the true brightness value, the following formula is used to cancel the drift value:

$$X=\{(A+s)-(B+2s)-(C+3s)+(D+4s)\}/2=(A-B-C+D)/2$$

where X denotes the brightness after correction, s is the drift, A to D are the values of brightness obtained under the voltage pattern described earlier. By averaging the differences between the brightness values of frames A and B, and between frames C and D, the drift component is nullified.

In the next step S6, the absolute values of the corrected brightness value are subjected to scaling transformations. The scaling transformation step involves converting the brightness data into voltage data. The process involves the use of the previously obtained offset and gain values, according to offset and gain calibrations described above, to obtain linear approximations of the conversions. That is, the gain corresponds with the slope of the linear equation, and the offset with the intercept of the equation.

In the next step S7, the screen images are clarified by space averaging treatment. This treatment consists of taking 3×3 pixel elements of the recording device, and using this cell as the central image data (value), and making corrections to the neighboring image data values, to the top, bottom, left, right, top left and right, bottom left and right data, according to the central value. For example, all the eight neighboring data are given the same weight as the central data. This smoothing step removes noise from the screen.

In the next step S8, image data is treated to assign the data binary values. That is, the voltage values associated with every pixel above a certain threshold value are given "0" and those below the value are given "1", to separate all the pixel data into two high-low groups.

In the next step S9, the binary valued data and the pixels map are subjected to "AND" analysis. The pixel map refers to a latticed pattern of the pixels in the LC display substrate 5. In this step, the pixels map is superimposed on top of the binary valued pixel results obtained in step 8 by an "AND" analysis. This binary value processing is carried out in order to correlate the pixels in the substrate 5 with those in the recording camera 3. For example, a pixel cell in the LC display substrate 5 corresponds with the 3×3 pixel elements of the recording device.

In the next step S10, the process of identifying defective pixel cells from the high-low image data of the LC display substrate 5 is carried out. The defective cells are those pixel cells, defined by the 3×3 pixels of the recording device, whose central pixel's binary value is "1." In other words, those pixels whose threshold value does not reach the set value. The results are stored in memory and the program proceeds to step S11, in which the identification ID is incremented by one, and the program proceeds to step S12, which examines whether the ID is 4 or not. In this instance it is 2, therefor the path in this step S12 is "No" and the program returns to step S4 and repeats the steps S4–S11. By this process, the defective pixel cells in camera 3-2 are identified. The program repeats the above steps for the cameras 3-3 and 3-4 until step S12 becomes "Yes".

Once the path in step S12 is "Yes" the program proceeds to step S13. The number of cameras determines the number of IDs in step S12. In step S13, the defective pixel data from cameras 3-1 to 3-4 are synthesized into a composite defective pixels result for the entire substrate 5 in terms of their size and distribution. Next, the screen prompts the operator to direct whether or not next frame sampling operation is to be performed. If further analysis is required, the operator enters "yes" and the program returns to step S1 and repeats the whole process all over. If the answer is "no" the analysis program is brought to an end.

As described above, the testing apparatus is able to provide the results of pixel defect analysis in one screen regardless of the size of the LC display substrate 5, and moreover, since the analysis is computerized, the results can be provided rapidly and automatically. Further, since the results are quantitative and are "in-process", i.e., obtained during processing steps, corrective actions can be taken as to increase the yield.

The above example utilized bias voltage of a certain pattern, it is also possible to utilize modulated frequencies. In this instance, defective pixels could be detected in terms of the changes in the brightness of the pixels, or for example, decay time constants of the change.

What is claimed is:

1. A method for testing imaging defects in a liquid crystal display substrate, said liquid crystal display substrate comprising a plurality of pixels, said method comprising the steps of:

applying an electric impulse signal between said pixels and an electro-optical element;

recording the responses of said electro-optical element with a plurality of recording means in synchronization with said application of electric signal to provide a frame data recording;

storing said recording in a memory device;

varying the magnitude and polarity of said electric signal and applying the changed signal between said pixels and said electro-optical element;

recording the responses of said array to said changes in changed signal to produce further frame data and storing said recording of further frame data;

repeating the above steps to provide a plurality of frame data recordings;

recalling said recordings frame at a time from memory;

subjecting said frame data to image analysis processing whereby defective pixels are identified from the response characteristics of said electro-optical element to changes in the applied signal.

2. The method of claim 1 wherein each of said plurality of recording means is a CCD-type camera.

3. The method of claim 1 further comprising a step of constructing quantity and distribution information from said frame data.

4. The method of claim 1 wherein said electric impulse signal is from a pattern generator.

5. The method of claim 1 wherein said plurality of pixels include more than about 1,000,000 pixels.

6. The method of claim 1 wherein said plurality of pixels include more than about 500,000 pixels.

7. A method for testing liquid crystal display substrate comprising the steps of:

employing an electro-optical element having a first and second side, said first side of said electro-optical element being coated with a transparent conductive layer, said second side of said electro-optical element being coated with a non-conductive, reflective material, said electro-optical element appearing non-transparent in the absence of an electric field across it;

employing a liquid crystal display substrate to be tested having first and second sides, said first side having a plurality of gate, source, and drain lines, and pixel elements;

placing said element-optical directly over, and immediately adjacent to said liquid crystal display substrate, such that the second side of said electro-optical element is facing, and slightly separated from said first side of said liquid crystal display substrate;

connecting a first terminal of a voltage source to said transparent conductive layer on said first side of said electro-optical element, connecting a second terminal of said voltage source to said source lines and connecting a third terminal of said voltage source to said drain lines formed on said liquid crystal display substrate, said first terminal servicing as a common reference voltage, said second and third terminals being independently controllable;

irradiating a beam of light from above said electro-optical element, such that said beam of light irradiates said first side of said electro-optical element;

applying a voltage between said transparent conductive element on said first side of said electro-optical element, and said gate and/or source lines on said liquid crystal display substrate, such that a voltage difference is generated between the two which is of sufficient magnitude to create an electric field between said pixel elements and said transparent conductive element to cause said electro-optical element to appear transparent to said a radiated beam of light;

measuring the intensity of the light reflected off of said second side of said electro-optical element, such that a defective portion of said liquid crystal display substrate which fails to apply the voltage to pixel elements therein is detected;

utilizing a plurality of light detection apparatuses to detect the light reflected from said second surface of said electro-optical element; and merging the results observed by each of said light detection apparatuses to form a single electronic image representing the functioning and non-functional pixels of said liquid crystal display substrate.

8. The method for testing liquid crystal display substrate as described in claim 7 in which said beam of light irradiating said first surface of said electro-optical element is applied in a direction essentially perpendicular to said electro-optical element.

9. The method for testing liquid crystal display substrate as described in claim 7 in which the light reflected from said second side of said electro-optical element is reflected in a direction essentially perpendicular to said second surface of said electro-optical element.

10. The method for testing liquid crystal display substrate as described in claim 7 in which the light reflected by said second surface of said electro-optical elemetn is detected by a charge coupled device light detecting array.

11. The method for testing liquid crystal display substrate as described in claim 7 and further comprising the steps of repeating the test for light reflected by said second surface of said electro-optical element a plurality of times in order to eliminate noise, bias, calibration, and other variations between similar electro-optical elements, cameras and other system variations are eliminated by averaging.

12. The method for testing liquid crystal display substrate as described in claim 7 in which said reflective layer is formed of a conductive material, divided up into discrete elements, one for each pixel element to be tested.

13. The method of claim 7 wherein said plurality of pixel elements include more than about 1,000,000 pixels.

14. A method for testing liquid crystal display substrate comprising the steps of:

employing a liquid crystal display substrate having first and second sides, said first side having a plurality of conductive lines and pixel elements;

placing an electro-optical element directly over, and immediately adjacent to said liquid crystal display substrate, such that a first, reflective side of said electro-optical element is facing, and slightly separated from said first side of said liquid crystal display substrate, said electro-optical element being essentially non-transparent when an electric field is not applied across it;

connecting a voltage source to an optically transparent electrode on a second side of said electro-optical element, and said conductive lines formed on said liquid crystal display substrate;

applying a beam of light from above said electro-optical element, such that said beam of light radiates said second side of said electro-optical element;

applying a voltage between said second side of said electro-optical element, and said conductive lines on said liquid crystal display substrate, such that a voltage difference is generated between the two which is of sufficient magnitude to generate an electric field, and cause said electro-optical element to become transparent to said a radiated beam of light;

measuring the light reflected off of said reflective side of said electro-optical element, such that a defective portion of said liquid crystal display substrate which fails to apply the voltage level to pixel elements therein is detected;

utilizing a plurality of light detection apparatuses to detect the light reflected from said reflective side of said electro-optical element; and merging the results observed by each of said light detection apparatuses to form a single electronic image displaying functional and non-functional sections of said liquid crystal display substrate.

15. The method for testing liquid crystal display substrate as described in claim 14 in which said beam of light irradiating said electro-optical element is applied in a direction essentially perpendicular to said electro-optical element.

16. The method for testing liquid crystal display substrate as described in claim 14 in which the light reflected from said reflective side of said electro-optical element is reflected in a direction essentially perpendicular to said reflective side of said electro-optical element.

17. The method for testing liquid crystal display substrate as described in claim 14 in which the light reflected by said reflective side of said electro-optical element is detected by a charge coupled device light detecting array.

18. The method for testing liquid crystal display substrate as described in claim 14 and further comprising the steps of repeating the test for light reflected by said reflective side of said electro-optical element a plurality of times in order to eliminate noise, bias, calibration, and other variations between similar electro-optical elements, cameras and other system variations are elminiated.

\* \* \* \* \*